United States Patent [19]

Slusarchyk et al.

[11] Patent Number: 4,681,937

[45] Date of Patent: Jul. 21, 1987

[54] 3-ACYLAMINO-2-OXO-1-AZETIDINYL ESTERS OF PHOSPHONIC ACIDS, PHOSPHORIC ACID AND PHOSPHORIC ACID ESTERS

[75] Inventors: William A. Slusarchyk, Belle Mead; Tamara Dejneka, Skillman; William H. Koster, East Amwell Township, Hunterdon County; Eric M. Gordon, Pennington, all of N.J.

[73] Assignee: E. R. Squibb & Sons, Inc., Princeton, N.J.

[21] Appl. No.: 424,132

[22] Filed: Sep. 27, 1982

[51] Int. Cl.$^4$ ...................... C07F 9/65; A61K 31/675
[52] U.S. Cl. .................................................. 540/355
[58] Field of Search ........................ 260/239 A, 245.4

[56] References Cited

U.S. PATENT DOCUMENTS 4,337,197 6/1982 Gordon et al. ................ 260/239 A

FOREIGN PATENT DOCUMENTS 857284 1/1978 Belgium .
0053815 6/1982 European Pat. Off. .
0053816 6/1982 European Pat. Off. .
2071650 9/1981 United Kingdom .

OTHER PUBLICATIONS

Clauss et al., Justus Liebigs Ann. Chem., 4:539–560 (1974).
Campbell, J. Chem. Soc., Chem. Comm., 15:730–731 (1980).
Zamboni et al., Can. J. Chem., 57:1945–1948 (1979).
Grechkin et al., (Chemical Abstracts 58:2418e), (1962).
Grechkin et al., (Chemical Abstracts 63:6939e), (1965).
Grechkin et al., (Chemical Abstracts 66:55295t), (1966).
Gray et al., J. Org. Chem., 44:1768–1771, (1979).
Buchanan, Can. J. Chem., 57:21–26, (1979).
Khamitov et al., Chem. Abs. 66,115768, (1967).

*Primary Examiner*—Mark L. Berch
*Attorney, Agent, or Firm*—Lawrence S. Levinson; Donald J. Barrack

[57] ABSTRACT

Antimicrobial activity is exhibited by β-lactams having a

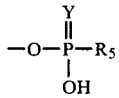

substituent in the 1-position and an acylamino substituent in the 3-position, or a pharmaceutically acceptable salt thereof; wherein Y is oxygen or sulfur and $R_5$ is hydroxyl, alkyl, substituted alkyl, phenyl, substituted phenyl, alkoxy, alkylthio, (substituted alkyl)oxy, (substituted alkyl)thio, phenyloxy, phenylthio, (substituted phenyl)oxy or (substituted phenyl)thio.

22 Claims, No Drawings

3-ACYLAMINO-2-OXO-1-AZETIDINYL ESTERS OF PHOSPHONIC ACIDS, PHOSPHORIC ACID AND PHOSPHORIC ACID ESTERS

RELATED APPLICATION

U.S. patent application Ser. No. 358,140, filed Mar. 15, 1982 U.S. Pat. No. 4,478,749 discloses β-lactam antibiotics having an acylamino substituent in the 3-position and a

substituent in the 1-position wherein $R_a$ is hydrogen, alkyl, substituted alkyl, phenyl or substituted phenyl and $R_b$ is hydroxy, alkoxy, (substituted alkyl)oxy, phenyloxy, (substituted phenyl)oxy, alkyl, substituted alkyl, phenyl, substituted phenyl, heteroaryl, amino-(—NH$_2$), substituted amino, alkylthio, (substituted alkyl)thio, phenylthio, (substituted phenyl)thio, 1-(ethoxycarbonyloxy)ethoxy, 1,3-dihydro-3-oxo-1-isobenzofuranyloxy,

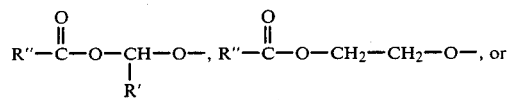

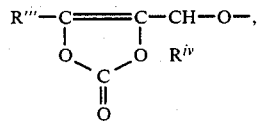

wherein R' is hydrogen or alkyl, R" is alkyl or phenyl, R''' is hydrogen, methyl or phenyl, and $R^{iv}$ is hydrogen or together with R''' is —(CH$_2$)$_3$— or —(CH$_2$)$_5$—.

U.S. patent application Ser. No. 381,260, filed May 24, 1982 discloses analogous β-lactams having a

substituent.

BACKGROUND OF THE INVENTION

The β-lactam ring,

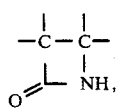

has been known since the late nineteenth century. While knowledge of β-lactam chemistry developed during the early 1900's, it was not until 1929 that Fleming reported in Brit. J. Exper. Pathol., 10, 226 (1929) that a fermentation product of the organism Penicillium notatum had antibiotic properties. The compound which Fleming had worked with was benzylpenicillin,

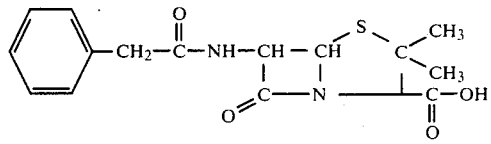

The in vivo activity of benzylpenicillin against various bacteria was reported by Chain et al. in Lancet, 2: 226 (1940).

During the early 1940's research in the field of penicillins was intense. This research focused first on structure elucidation and then on synthetic routes for preparing benzyl penicillin. It was not, however, until the late 1950's that a totally synthetic route was discovered for the preparation of benzyl penicillin.

U.S. Pat. No. 2,941,955, issued June 21, 1960, to Doyle et al., discloses the discovery of 6-aminopenicillanic acid,

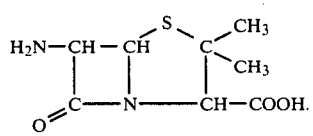

This patent was followed by U.S. Pat. No. 2,951,839, issued Sept. 6, 1960, also to Doyle et al., which discloses the use of 6-aminopenicillanic acid as a valuable intermediate which could be acylated, using art-recognized procedures, to obtain penicillin derivatives having antibiotic properties. Using 6-aminopenicillanic as a stepping stone, research chemists have prepared numerous penicillin derivatives having antibiotic activity.

The second major class of β-lactam antibiotics is the cephalosporins. In the 1940's a Cephalosporium species was found to produce an antibiotic that had activity against gram-positive and gram-negative bacteria. Work in the 1950's showed that the fermentation product of a Cephalosporium species contained not one, but several antibiotics. One of these antibiotics, cephalosporin C,

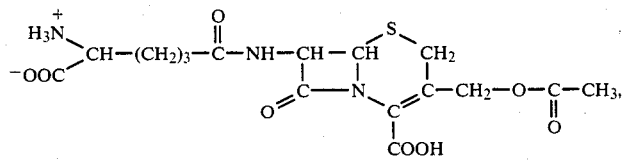

proved to be an important stepping stone in cephalosporin research. Removal of the acyl group in the 7-position of cephalosporin C yields 7-aminocephalosporanic acid,

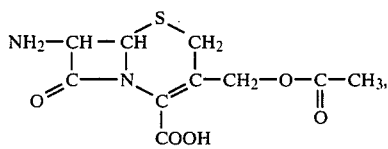

an intermediate useful for the preparation of numerous acylated compounds which are analogs of cephalosporin C.

The penicillins and cephalosporins are, of course, the most important of the β-lactam antibiotics reported to date. Others have, however, been reported. Stapley et al., *Antimicrobial Agents and Chemotherapy*, 2(3): 122 (1972) disclose that certain actinomycete cultures isolated from soil produce antibiotics characterized by a methoxy group and D-α-aminoadipic acid on the 7-carbon of the cephem nucleus. The cephamycins, as they are known, have the formula

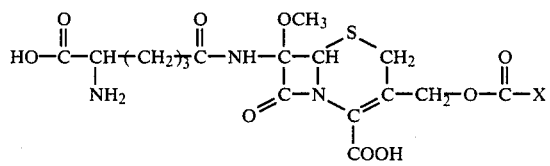

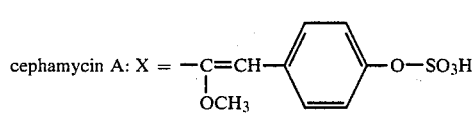

cephamycin B: X =

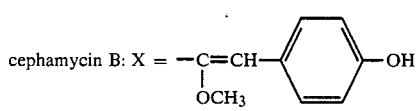

cephamycin C: X = —NH$_2$.

Stapley et al. reported that cephamycin A and cephamycin B each exhibits a similar range of potencies against gram-negative and gram-positive bacteria, and cephamycin C had greater potency against gram-negative bacteria than against gram-positive bacteria. Cephamycin C was reported to be the most active of the three antibiotics.

Scannell et al., *The Journal of Antibiotics*, XXVII (1): 1 (1975), disclose the isolation from a fermentation broth of Streptomyces species 372A of (S)-alanyl-3-[α-(S)-chloro-3-(S)-hydroxy-2-oxo-3-azetidinyl-methyl]-(S)-alanine, which has the formula

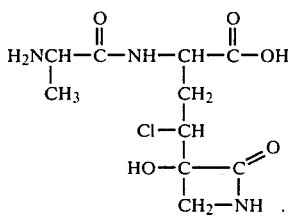

The structure of the above naturally occurring monocyclic β-lactam containing molecule is similar to the structure of the earlier discovered β-lactam containing molecules known as tabotoxins, i.e.,

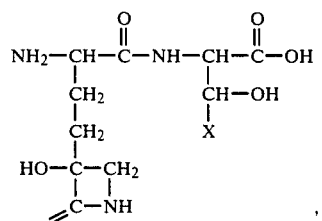

wherein X is hydrogen or methyl as reported by Stewart, *Nature*, 229: 174 (1971), and Taylor et al., *Biochem. Biophys. Acta.*, 286: 107 (1972).

Recently, several novel series of naturally occurring β-lactam antibiotics have been isolated. The nocardicins, nocardicin A and B, are monocyclic β-lactams having the formula

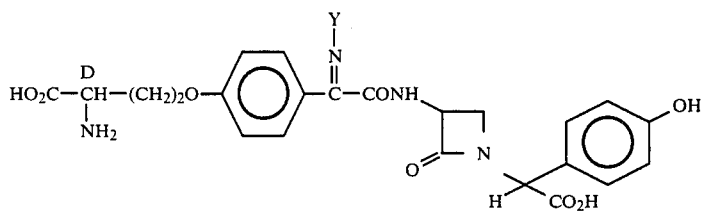

nocardicin A: Y = —syn(Z)OH
nocardicin B: Y = —anti(E)OH, as reported by Hashimoto et al., *The Journal of Antibiotics*, XXIX (9): 890 (1976).

Clavulanic acid, a bicyclic β-lactam antibiotic isolated from fermentation broths of *Streptomyces clavuligerus*, has the formula

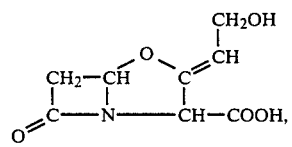

i.e., Z-(2R,5R)-3-(β-hydroxyethylidene)-7-oxo-4-oxa-1-azabicyclo[3,2,0]heptane-2-carboxylic acid, as reported by Lloyd et al., *J.C.S. Chem. Comm.*, 266 (1976).

Still another recently isolated β-lactam antibiotic is thienamycin, an antibiotic isolated from the fermentation broths of *Streptomyces cattleya*. As reported by Albers-Schonberg et al., *J.A.C.S.*, 100: 20, 6491 (1978), thienamycin has the structure

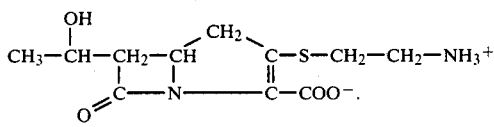

Additional fused β-lactams, olivanic acid derivatives, have recently been isolated from cultures of *Streptomyces olivaceus*. As disclosed by Brown et al., *J.C.S. Chem. Comm.*, these olivanic acid derivatives have the formulas

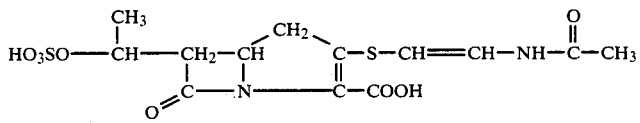

and

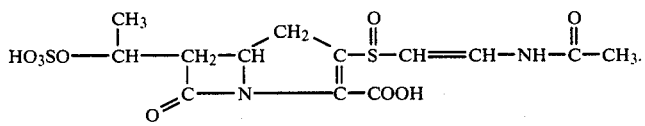

The isolation of the above antibiotics, and a discussion of their activity, is reported by Butterworth et al., *The Journal of Antibiotics*, XXXII (4): 294 (1979) and by Hood et al., *The Journal of Antibiotics*, XXXII (4): 295 (1979).

Another recently isolated β-lactam antibiotic is PS-5, reported by Okamura et al., *The Journal of Antibiotics*, XXXI: 480 (1978) and *The Journal of Antibiotics*, XXXII (4): 262 (1979). The structure of this antibiotic, which is produced by *Streptomyces cremeus* subspecies *auratilis*, is reported to be

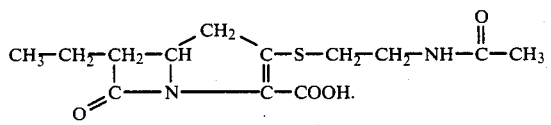

Structurally related antibiotics PS-6 and PS-7 are reported in European Patent application Ser. No. 1,567 to have the respective structures

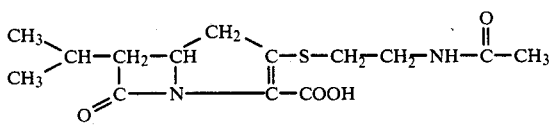

and

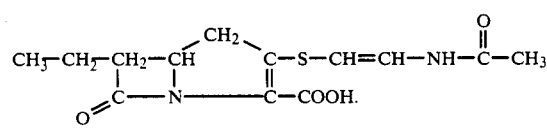

Two recently disclosed series of β-lactam antibiotics are the monocyclic β-lactams having the formulas

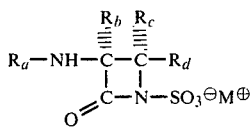

and

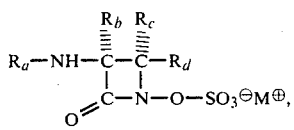

wherein $R_a$ is acyl, $R_b$ is hydrogen or alkoxy, $R_c$ and $R_d$ are various organic substituents, and $M^{\ominus}$ is a cation. The antibiotics having an $-SO_3^{\oplus}M^{\ominus}$ activating group are disclosed in U.K. patent application No. 2,071,650, published Sept. 23, 1981. The antibiotics having an $-O-SO_3^{\oplus}M^{\ominus}$ activating group are disclosed in U.S. Pat. No. 4,337,197, issued June 29, 1982.

BRIEF DESCRIPTION OF THE INVENTION

This invention is directed to a novel family of β-lactam antibiotics, and to the use of such compounds as antibacterial agents. It has been discovered that the β-lactam nucleus can be biologically activated by a substituent having the formula

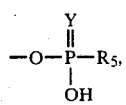

and pharmaceutically acceptable salts thereof, attached to the nitrogen atom in the nucleus.

β-Lactams having a

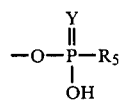

substituent (or a pharmaceutically acceptable salt thereof) in the 1-position and an acylamino substituent in the 3-position exhibit activity against a range of gram-negative and gram-positive bacteria.

Illustrative members of the novel family of β-lactam antibiotics of this invention are those encompassed by the formula

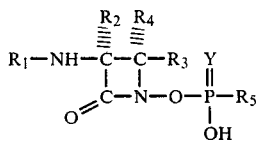

or a pharmaceutically acceptable salt thereof.

As used in formula I and throughout the specification, the symbols are as defined below.

$R_1$ is acyl;

$R_2$ is hydrogen or methoxy;

$R_3$ and $R_4$ are the same or different and each is hydrogen, alkyl, alkenyl, alkynyl, cycloalkyl, phenyl, substituted phenyl or a 4,5,6 or 7-membered heterocycle (referred to hereinafter as $R_6$) or one of $R_3$ and $R_4$ is hydrogen and the other is azido, halomethyl, dihalomethyl, trihalomethyl, alkoxycarbonyl, 2-phenylethenyl, 2-phenylethynyl, carboxyl,

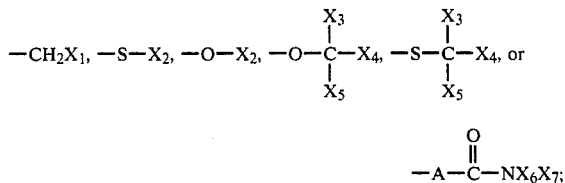

$X_1$ is azido, amino (—NH$_2$), hydroxy, alkanoylamino, alkylsulfonyloxy, phenylsulfonyloxy, (substituted phenyl)sulfonyloxy, phenyl, substituted phenyl, cyano, —S—$X_2$ or —O—$X_2$;

$X_2$ is alkyl, substituted alkyl, phenyl, substituted phenyl, phenylalkyl, (substituted phenyl)alkyl, alkanoyl, substituted alkanoyl, phenylcarbonyl, (substituted phenyl)carbonyl or heteroarylcarbonyl;

one of $X_3$ and $X_4$ is hydrogen and the other is hydrogen or alkyl, or $X_3$ and $X_4$ when taken together with the carbon atom to which they are attached form a cycloalkyl group;

$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

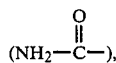

(substituted amino)carbonyl, or cyano (—C≡N);
A is —CH=CH—, —CH$_2$—CH=CH—, —(CH$_2$)$_n$—, —(CH$_2$)$_{n'}$—O—, —(CH$_2$)$_{n'}$—NH—, or —(CH$_2$)$_{n'}$—S—CH—$_2$;

n is 0, 1, 2 or 3;

n' is 1 or 2;

$X_6$ and $X_7$ are the same or different and each is hydrogen or alkyl, or $X_6$ is hydrogen and $X_7$ is amino, substituted amino, acylamino or alkoxy;

$R_5$ is hydroxyl, alkyl, substituted alkyl, phenyl, substituted phenyl, alkoxy, alkylthio, (substituted alkyl)oxy, (substituted alkyl)thio, phenyloxy, phenylthio, (substituted phenyl)oxy or (substituted phenyl)thio; and Y is oxygen or sulfur.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one, or more, azido, amino (—NH$_2$), halogen, hydroxy, carboxy, cyano, alkoxycarbonyl, aminocarbonyl, alkanoyloxy, alkoxy, phenyloxy, (substituted phenyl)oxy, $R_6$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "protected carboxyl" refers to a carboxyl group which has been esterified with a conventional acid protecting group. These groups are well known in the art; see, for example, U.S. Pat. No. 4,144,333, issued Mar. 13, 1979. The preferred protected carboxyl groups are benzyl, benzhydryl, t-butyl, p-methoxybenzyl, and p-nitrobenzyl esters.

The term "substituted phenyl" refers to a phenyl group substituted with 1, 2 or 3 amino(—NH$_2$), halogen, hydroxyl, trifluoromethyl, alkyl (of 1 to 4 carbon atoms), alkoxy (of 1 to 4 carbon atoms), or carboxyl groups.

The expression "a 4,5,6 or 7-membered heterocycle" (referred to as "$R_6$") refers to substituted and unsubstituted, aromatic and non-aromatic groups containing one or more nitrogen, oxygen or sulfur atoms. Exemplary substituents are oxo(=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furylimino

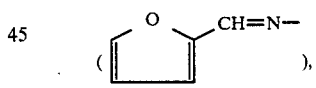

benzylimibn and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetincyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4,5,6 or 7-membered heterocycles are 1-alkyl-3-azetinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2- aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)-amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-furanyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NY$_1$Y$_2$ wherein Y$_1$ is hydrogen, alkyl, phenyl, substituted phenyl, phenylalkyl or (substituted phenyl)alkyl, and Y$_2$ is alkyl, phenyl, substituted phenyl, phenylalkyl, (substituted phenyl)alkyl, hydroxy, cyano, alkoxy, phenylalkoxy, or amino (—NH$_2$).

The term "substituted alkanoyl" includes within its scope compounds having the formula (substituted alkyl)

(wherein "substituted alkyl" is defined above ) and phenylalkanoyl.

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins,* edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894 published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein R$_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

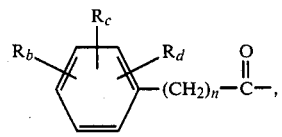

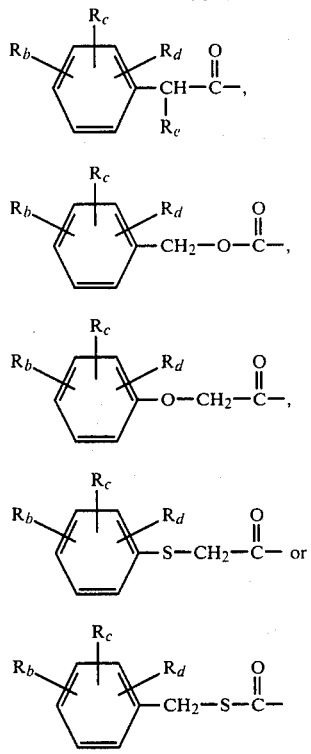

wherein n is 0, 1, 2 or 3; R$_b$, R$_c$, and R$_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and R$_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

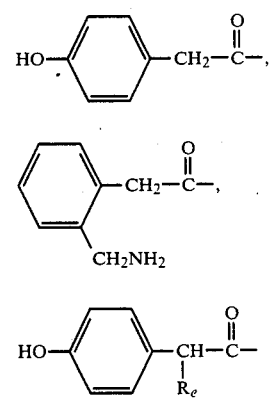

(R$_e$ is preferably a carboxyl salt or sulfo salt) and

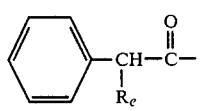

(R$_e$ is preferably a carboxyl salt or sulfo salt).

(c) Heteroaromatic groups having the formula

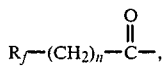

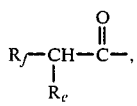

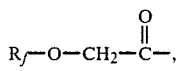

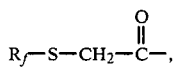

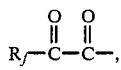

wherein n is 0, 1, 2 or 3; $R_e$ is as defined above; and $R_f$ is a substituted or unsubstituted 5-, 6- or 7-membered heterocyclic ring (heteroaryl group) containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

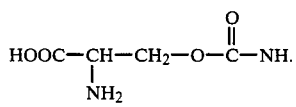

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

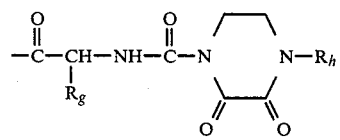

wherein $R_g$ is an aromatic group (including carbocyclic aromatics such as those of the formula :

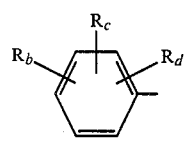

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

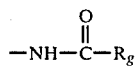

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oxyimino)arylacetyl groups having the formula

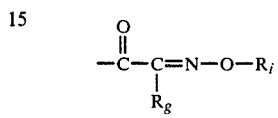

wherein $R_g$ is as defined above and $R_i$ is hydrogen, $R_6$, alkyl, cycloalkyl, alkylaminocarbonyl, arylaminocarbonyl (i.e.,

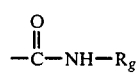

wherein $R_g$ is as defined above) or substituted alkyl (wherein the alkyl group is substituted with 1 or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

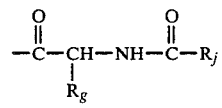

wherein $R_g$ is as defined above and $R_j$ is

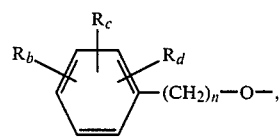

amino, alkylamino, (cyanoalkyl)amino, amido, alkylamido, (cyanoalkyl)amido,

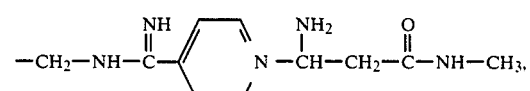

-continued

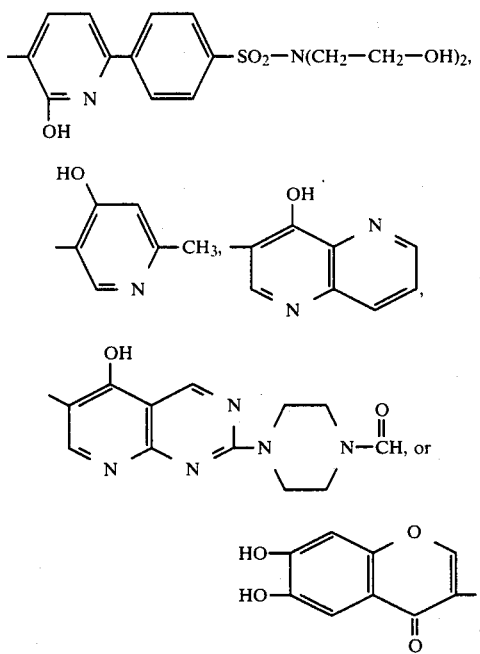

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl-]amino]arylacetyl groups having the formula

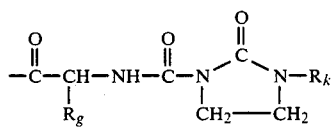

wherein $R_g$ is as defined above and $R_k$ is hydrogen, alkylsulfonyl, arylmethyleneamino (i.e., —N=CH—$R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The terms "salt" and "salts" refer to basic salts formed with inorganic and organic bases. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, e.g., in isolating or purifying the product.

The salts are formed in conventional manner by reacting the free acid form of the product with one or more equivalents of the appropriate base providing the desired cation is in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

β-Lactams having a

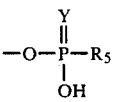

substituent (or a pharmaceutically acceptable salt thereof) in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins, (e.g., cephamycin C).

With respect to the preferred β-lactams of formula I, the structural formulas have been drawn to show the stereochemistry at the chiral center in the 3-position. Because of the nomenclature convention, those compounds of formula I wherein $R_2$ is hydrogen have the S-configuration and those compounds of formula I wherein $R_2$ is methoxy have the R-configuration.

Also included within the scope of this invention are racemic mixtures which contain the above-described β-lactams.

DETAILED DESCRIPTION OF THE INVENTION

β-Lactams having a

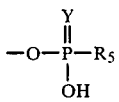

substituent (or a pharmaceutically acceptable salt thereof) in the 1-position of the β-lactam nucleus and an acylamino substituent in the 3-position of the β-lactam nucleus have activity against a range of gram-negative and gram-positive organisms.

The

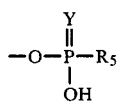

substituent (or a pharmaceutically acceptable salt thereof) is essential to the activity of the compounds of this invention.

The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

The β-lactams of this invention can be prepared from hydroxamic acids of formula VIII (infra.), which are obtainable from an amino acid having the formula

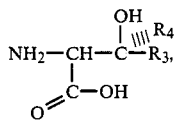  II utilizing the methodology disclosed in U.S. Pat. No. 4,337,197. As disclosed therein, the amino group is first protected with a classical protecting group (e.g., t-butoxycarbonyl, benzyloxycarbonyl, o-nitrophenylsulfenyl, etc.), yielding a compound having the formula

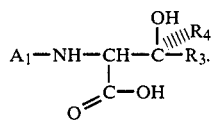  III

In formula III, and throughout the specification, the symbol "$A_1$" refers to a nitrogen protecting group.

The carboxyl group of a protected amino acid of formula III is then reacted with an amine salt having the formula

  IV

In formula IV, and throughout the specification, the symbol "$Y_3$" refers to benzyl, pivaloyl, —CH$_2$(NHA)-CO$_2$alkyl, t-butyl, p-nitrobenzyl, benzhydryl, 2-cyanoethyl, 2-trimethylsilylethyl, trichloroethyl, inter alia. The reaction proceeds in the presence of a coupling agent such as 1-ethyl-3-(3-dimethylaminopropyl)carbodiimide or dicyclohexylcarbodiimide, and yields a compound having the formula

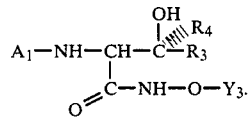  V

The hydroxyl group of a compound of formula V is converted to a leaving group, using, for example, a classical reagent such as methanesulfonyl chloride (methanesulfonyl is referred to hereinafter as "Ms").

The fully protected compound having the formula

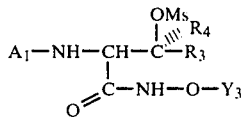  VI is cyclized by treatment with base, e.g., potassium carbonate. The reaction is preferably carried out in an organic solvent such as acetone, under reflux conditions, and yields a compound having the formula

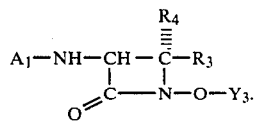  VII

Alternatively, cyclization of a compound of formula V can be accomplished without first converting the hydroxyl group to a leaving group. Treatment of a compound of formula V with triphenylphosphine and diethylazodicarboxylate or carbon tetrachloride, triphenylphosphine and a base such as triethylamine, yields a compound of formula VII.

Both of the methods disclosed above for ring closure of a compound of formula V result in the inversion of the stereochemistry at the carbon bonded to the $R_3$ and $R_4$ substituents.

Selective reduction of a compound of formula VII (using catalytic hydrogenation if $Y_3$ is benzyl or by treatment with a base such as sodium sulfide or sodium hydroxide if $Y_3$ is pivaloyl or with DBU if $Y_3$ is —CH$_2$CH(NHA)CO$_2$alkyl) yields the corresponding compound having the formula

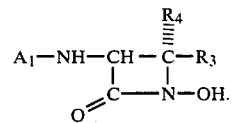  VIII

Phosphorylation of a hydroxamic acid of formula VIII can be accomplished by first treating the compound with base (e.g., 2,6-lutidine or triethylamine) to generate the corresponding anion and then reacting the salt with a phosphorous derivative having the formula

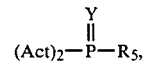  IX wherein the activating group "Act" is, most preferably, chlorine to yield the corresponding compound having the formula

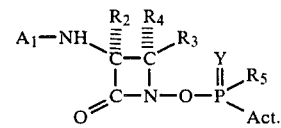  X

Hydrolysis of a compound of formula X under neutral or mildly acidic conditions yields the corresponding compound having the formula

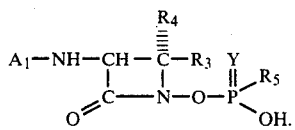  XI

Alternatively, phosphorylation of a hydroxamic acid of formula VIII can be accomplished by first treating the compound with a base (e.g., 2,6-lutidine) and then reacting it with a phosphorous derivative having the formula

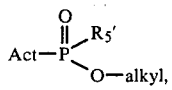  XII wherein $R_5'$ is alkyl or alkoxy, to obtain the corresponding compound having the formula

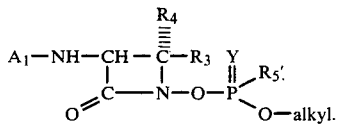  XIII

Treatment of a compound of formula XIII with an acid-scavenger and drying agent such as bis-trimethylsilylacetamide, followed by treatment with trimethylsilyl bromide, yields an intermediate silyl ester having the formula

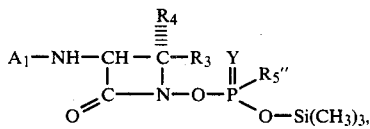  XIV wherein $R_5''$ is alkyl or $-O-Si(CH_3)_3$. A compound of formula XIV is readily converted to a salt of the corresponding compound of formula XI by treatment with aqueous buffer in the range of pH 2.5 to pH 6, with or without an alcohol.

Deprotection of the 3-amino substituent of a compound of formula XI can be accomplished using art-recognized techniques. If, for example, the protecting group is t-butoxycarbonyl, trifluoroacetic acid-anisole can be used to deprotect the amino group. If the protecting group is benzyloxycarbonyl, catalytic (e.g., palladium on charcoal) hydrogenation can be used. If the protecting group is o-nitrophenylsulfenyl, p-toluenesulfonic acid can be used in combination with p-thiocresol. The deprotected compound has the formula

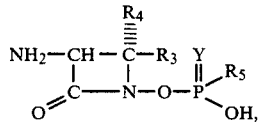  XV and is a key intermediate for preparing the compounds of this invention.

Well known acylation techniques can be used to convert a compound of formula XV to the corresponding compound having the formula

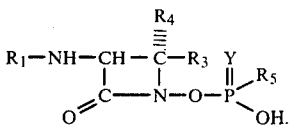  XVI

Exemplary techniques include reaction with a carboxylic acid ($R_1$—OH) or corresponding carboxylic acid halide or carboxylic acid anhydride. The reactions with a carboxylic acid proceed most readily in the presence of a carbodiimide such as dicyclohexylcarbodiimide and a substance capable of forming a reactive intermediate in situ such as N-hydroxybenzotriazole or 4-dimethylaminopyridine. In those instances wherein the acyl group ($R_1$) contains reactive functionality (such as amino or carboxyl groups) it may be necessary to first protect these functional groups, then carry out the acylation reaction, and finally deprotect the resulting product.

The products of formula I wherein $R_2$ is methoxy can be prepared from the corresponding compound of formula XI wherein $A_1$ is benzyloxycarbonyl. Halogenating (preferably chlorinating) the amide nitrogen of a compound of formula XI yields a compound having the formula

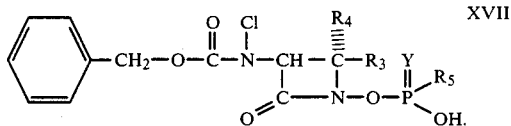  XVII

Reagents and procedures of N-chlorinating amides are known in the art. Exemplary reagents are tert.-butyl hypochlorite, sodium hypochlorite, and chlorine. The reaction can be run in an organic solvent (e.g., a lower alkanol such as methanol) or in a two phase solvent system (e.g., water/methylene chloride) in the presence of a base such as sodium borate decahydrate. The reaction is preferably run at a reduced temperature.

Reaction of a compound of formula XVII with a methoxylating agent, e.g., an alkali metal methoxide, yields a compound (in combination with its enantiomer if $R_3$ and $R_4$ are the same or if XVII is a racemic mixture) having the formula

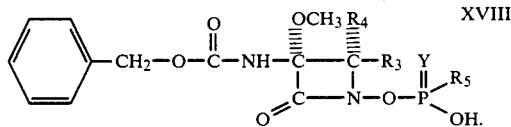  XVIII

The reaction can be run in an organic solvent, e.g., a polar organic solvent such as tetrahydrofuran, at a reduced temperature.

Alternatively, a compound of formula XI, wherein $A_1$ is benzyloxycarbonyl, can be converted to a compound of formula XVIII using a single step procedure. The methoxylating agent can first be mixed with a compound of formula XI and the N-chlorinating reagent then added to the reaction mixture.

Conversion of a compound of formula XVIII to the desired products of formula I can be accomplished using the procedures described above for the conversion of an intermediate of formula XI to a product of this invention.

The following examples are specific embodiments of this invention.

EXAMPLE 1

Methylphosphonic acid, [3S-[3α(Z),4β]]-3-[[(2-amino-4-thiazolyl)(methoxyimino)acetyl]amino]-4-methyl-2-oxo-1-azetidinyl ester, potassium salt (A) O-Benzyl-α-N-t-butoxycarbonyl-L-threonine hydroxamate To a stirred solution of 10.95 g (50 mmol) of N-t-butoxycarbonyl-L-threonine in 50 ml of water was added a solution of 8.75 g (55 mmol) of O-benzylhydroxylamine hydrochloride and 50 ml of water, which had been adjusted to pH 4.0 using 2N KOH. After the addition, the pH was adjusted to 4.0, and a solution of 10.55 g (55 mmol) of 1-ethyl-3-[(3-dimethylamino)-propyl]carbodiimide hydrochloride (water soluble carbodiimide, in 50 ml of water was added over 10 minutes while maintaining the pH at 4.0–4.5 using 1N HCl. The reaction was continued for 20 minutes in this pH range, and then extracted with ethyl acetate. The ethyl acetate extract was washed at pH 8.5 (aqueous NaHCO$_3$) and then at pH 3.0 (1N HCl), dried (Na$_2$SO$_4$), and evaporated to a crystalline residue. Treatment with ethyl acetate-hexane gave 9.60 g of crystalline product.

(B) O-Benzyl-α-N-t-butoxycarbonyl-L-(O-mesyl-threonine)hydroxamate

To a stirred solution of O-benzyl-α-N-t-butoxycarbonyl-L-threonine hydroxamate (0.60 g, 29.6 mmol) in 24 ml of dry pyridine at 0°–5° C. under nitrogen was added dropwise 2.63 ml (34 mmol) of methylsulfonyl chloride. The reaction was stirred at this temperature for 4 hours, poured into 250 ml of water, adjusted to pH 3.5 (3N HCl), treated with saturated NaCl solution, and extracted repeatedly with ethyl acetate. The combined ethyl acetate extract was washed with water, then water at pH 7, dried (Na$_2$SO$_4$), and evaporated to give 11.68 g of desired product as a crystalline mass.

(C) [3S-(3α,4β)]-3-[[(1,1-Dimethylethoxy)carbonyl]amino]-4-methyl-2-oxo-1-(phenylmethoxy)azetidine Potassium carbonate (12 g, 0.087 mol) was added to a stirred solution of 11.65 g (0.029 mol) of O-benzyl-α-N-t-butoxycarbonyl-L-(O-mesylthreonine)hydroxamate in 490 ml of acetone under nitrogen and the reaction was refluxed. After 6 hours, the reaction mixture was cooled and filtered through Celite. Evaporation of the filtrate gave a crystalline residue, which was recrystallized from ethyl acetate-hexane to give 4.65 g of crystalline product.

(D) [3S-(3α,4β)]-3-[[(1,1-Dimethylethoxy)carbonyl]amino]-4-methyl-2-oxo-1-hydroxyazetidine To a solution of [3S-(3α,4β)]-3-[[(1,1-dimethylethoxy)carbonyl]amino]-4-methyl-2-oxo-1-(phenylmethoxy)azetidine (1.22 g, 4 mmole) in 40 ml of methanol was added 10% palladium on charcoal (0.8 g), and the reaction mixture ws reduced at atmospheric pressure for 15 minutes (until hydrogen uptake stopped). The reaction mixture was filtered through Celite and concentrated in vacuo. The solid that was obtained, was dried over P$_2$O$_5$ at 45° C. to yield 0.75 g of product.

(E) Methylphosphonic acid, [3S-(3α,4β)]-3-[[(1,1-dimethylethoxy)carbonyl]amino]-4-methyl-2-oxo-1-azetidinyl ester, potassium salt

[3S-(3α,4β)]-3-[[(1,1-Dimethylethoxy)carbonyl]amino]-4-methyl-2-oxo-1-hydroxyazetidine (1.02 g, 4.7 mmole) was partially dissolved in 14 ml of dry dichloromethane and cooled to −10° C. under nitrogen. 2,6-Lutidine (0.6 ml, 4.9 mmole) was then added followed by the dropwise addition of methylphosphonic dichloride (0.62 g, 4.6 mmole) in 5 ml of dichloromethane. After addition, the reaction was stirred at −10° C. for 1 hours. The temperature was allowed to rise to 0° C., and then 20 ml of 0.5M KH$_2$PO$_4$ containing 2 ml of 2N KOH and 15 ml of tetrahydrofuran was added (pH 6.6). This solution was stirred at 0°–15° C. for 5 hours, and the pH was maintained at 4.2 by the addition of 1N KOH. The reaction mixture was concentrated in vacuo to remove solvent and the remainder was lyophilized. The lyophilate was washed with two 200 ml portions of dichloromethane, and the dichloromethane was concentrated in vacuo to yield 1.63 g of crude material. This was dissolved in 5 ml of water (pH 4.5) and passed through 60 ml of Dowex 50 resin (K$^\oplus$, 0.7 meq/ml) to yield 1.03 g of crude product. The product was further purified by chromatography through 80 ml of HP-20 resin using water as eluent. The product which was found to elute in a wide band (500 ml) gave, after lyophilization, 0.4 g of hygroscopic material.

(F) Methylphosphonic acid, [3S-(3α,4β)]-3-amino-2-methyl-4-oxo-1-azetidinyl ester, trifluoroacetic acid salt Methylphosphonic acid, [3S-(3α,4β)]-3-[[(1,1-dimethylethoxy)carbonyl]amino]-4-methyl-2-oxo-1-azetidinyl ester, potassium salt (0.35 g, 1 mmole) was suspended in 1.5 ml of dichloromethane and 1.25 ml of anisole. The reaction mixture was cooled to −10° C., and trifluoroacetic acid (0.95 ml) was added. This was stirred under nitrogen at −10° C. for 1 hour. The reaction mixture was evaporated in vacuo to a residue, which was evaporated from toluene (twice) to give a viscous oil. Ether was added, and the oil solidified. The ether was decanted and the product was dried in vacuo.

(G) Methylphosphonic acid, [3S-[3α(Z),4β]]-3-[[(2-amino-4-thiazolyl)(methoxyimino)acetyl]amino]-4-methyl-2-oxo-1-azetidinyl ester, potassium salt 1-Hydroxybenzotriazole (0.169 g, 1.1 mmole) and (Z)-(2-amino-4-thiazolyl)(methoxyimino) acetic acid (0.223 g, 1.1 mmole) were dissolved in 3 ml of dry dimethylformamide under nitrogen. this was cooled to 0° C., and N,N'-dicyclohexylcarbodiimide (0.228 g, 1.1 mmole) was added portionwise. After addition, the reaction was stirred at 0° C. for 1 hour. To this was added a solution of methylphosphonic acid, [3S-(3α,4β)]-3-amino-2-methyl-4-oxo-1-azetidinyl ester, trifluoroacetic acid salt in 2 ml of dimethylformamide and 1.1 ml of N,N-diisopropylethylamine at 0° C. The reaction was stirred at 0° C. for 1 hour and then at room temperature overnight. The solution was filtered, and the filtrate was concentrated in vacuo. The residue was dissolved in water (pH 4.5), and the solution was washed with dichloromethane. The aqueous solution was passed through 80 ml of Dowex 50 (K$^\oplus$ 0.7 meq/ml). Partial purification of product was obtained by taking 8 ml fractions. Those fractions that contained product (4–8, 40 ml) were pooled and lyophilized to yield 0.4 g of material which was purified further by chromatography through 150 ml of HP-20 resin using water as eluent. Lyophilization gave 32 mg of desired product containing ca. 0.1–0.2 equivalents of 1-hydroxybenzotriazole; melting point 160°–180° C., dec.

Analysis Calc'd. for C$_{11}$H$_{15}$N$_5$O$_6$SPK: C, 31.81; H, 3.64; N, 16.86; S, 7.72; P, 7.46, Found: C, 30.24; H, 3.71; N, 16.22; S, 7.23; P, 5.6.

EXAMPLE 2

[3S-[3α(Z),4β]]-2-[[[1-(2-Amino-4-thiazolyl)-2-[[1-[(hydroxymethylphosphinyl)oxy]-4-methyl-2-oxo-3-azetidinyl]amino]-2-oxoethylidine]amino]oxy]-2-methylpropanoic acid, dipotassium salt (A) Methylphosphonic acid, [3S-(3α,4β)]-3-amino-4-methyl-2-oxo-1-azetidinyl ester, trifluoroacetic acid salt Methylphosphonic acid, [3S-(3α,4β)]-3-[[(1,1-dimethylethoxy)carbonyl]amino]-4-methyl-2-oxo-1-azetidinyl ester, potassium salt (0.223 g, 0.7 mmole; see example 1E) was suspended in 0.53 ml of anisole and 0.53 ml of dry dichloromethane under nitrogen. Trifluoroacetic acid (1.0 ml) was added dropwise at 0° C., and the reaction mixture was stirred at 0° C. to 5° C. for 2 hours. This was concentrated in vacuo to a residue, which was dried by concentration two times from 30 ml portions of toluene. The crude reaction product was triturated twice with ether to give, upon drying, a solid.

(B) [3S-[3α(Z),4β]]-2-[[[1-(2-Amino-4-thiazolyl)-2-[[1-[(hydroxymethylphosphinyl)oxy]-4-methyl-2-oxo-3-azetidinyl]amino]-2-oxoethylidine]amino]oxy]-2-methylpropanoic acid, diphenylmethyl ester, potassium salt (Z)-(2-Amino-4-thiazolyl)[[2-(diphenylmethoxy)-1,1-dimethyl-2-oxoethoxy]imino]acetic acid (0.310 g, 0.7 mmole) and 1-hydroxybenzotriazole (0.108 g, 0.7 mmole) were dissolved in 4 ml of dry dimethylformamide under nitrogen. This was cooled to 0° C., and N,N′-dicyclohexylcarbodiimide (0.145 g, 0.7 mmole) was added portionwise. After addition, the reaction was stirred at 0° C. for 1 hour. To this was added a solution of methylphosphonic acid, [3S-(3α,4β)]-3-amino-4-methyl-2-oxo-1-azetidinyl ester, trifluoroacetic acid salt (ca. 0.7 mmole) in 2 ml of dimethylformamide and 0.5 ml of N,N-diisopropylethylamine at 0° C. The reaction was stirred at 0° C. for 1 hour and then at room temperature overnight. The solution was filtered and the filtrate was concentrated in vacuo. The residue was dissolved in 50 ml of dichloromethane and washed with 2 ml of water (pH 4.5). The dichloromethane was concentrated in vacuo to yield 0.581 g of crude product. This was purified partially by dissolving in 20 ml of ethyl acetate and washing with 5 ml portions of $KH_2PO_4$ buffer at pH 4.5 (four times). The aqueous washes were lyophilized overnight to give 0.261 g of a residue which was passed through 10 ml of Dowex 50 (K⊕ 0.7 meq/ml) using water, and lyophilized to give 0.233 g of crude product contaminated with hydroxybenzotriazole.

(C) [3S-[3α(Z),4β]]-2-[[[1-(2-Amino-4-thiazolyl)-2-[[1-[(hydroxymethylphosphinyl)oxy]-4-methyl-2-oxo-3-azetidinyl]amino]-2-oxoethylidine]amino]oxy]-2-methylpropanoic acid, dipotassium salt

[3S-[3α(Z),4β]]-2-[[[1-(2-Amino-4-thiazolyl)-2-[[1-(hydroxymethylphosphinyl)oxy]-2-methyl-2-oxo-3-azetidinyl]amino]-2-oxoethylidine]amino]oxy-2-methylpropanoic acid, diphenylmethyl ester, potassium salt (0.223 g) was dissolved in 1.8 ml of dichloromethane, 0.5 ml of anisole, and 1.5 ml of trifluoroacetic acid, and stirred under nitrogen at 0° C. for 2 hours. The reaction mixture was concentrated in vacuo and evaporated from toluene twice. The residue was washed with ether:ethyl acetate (1:1) (three times) to give the trifluoroacetic acid salt as a white solid. This was dissolved in 1.5 ml of pH 4.5 0.5M $KH_2PO_4$, and the pH was adjusted to 6.5 with 1N KOH. This aqueous fraction was chromatographed through 80 ml of HP-20 resin with water to give 94 mg of desired product, melting point 60°–70° C.

Analysis Calc'd for $C_{14}H_{18}N_5O_8PS.2K.3.75H_2O$: C, 28.35; H, 4.33; N, 11.80; P, 5.22. Found: C, 28.61; H, 3.76; N, 11.45; P, 4.9.

EXAMPLE 3

Methylphosphonic acid, [3S-[3α(R),4β]]-3-[[[[(4-ethyl-2,3-dioxo-1-piperazinyl)carbonyl]amino]phenylacetyl]amino]-4-methyl-2-oxo-1-azetidinyl ester potassium salt (3S-trans)-3-[[[[(4-Ethyl-2,3-dioxo-1-piperazinyl)carbonyl]amino]phenylacetyl]amino]-1-hydroxy-4-methyl-2-azetidinone (0.22 g, 0.53 mmol; see U.S. Pat. No. 4,337,197) was suspended in 8 ml of dry dichloromethane at −10° C. under nitrogen. 2,6-Lutidine (0.07 ml, 0.6 mmol) was added followed by the dropwise addition of methylphosphonic dichloride in 0.5 ml of dichloromethane. After addition, the reaction was stirred at −10° C. for 2 hours. The temperature was allowed to rise to 0° C., 8 ml of 0.5M $KH_2PO_4$ containing 0.6 ml of 2N KOH (pH 6.6) was added and the reaction was stirred at room temperature for 2 hours. The organic layer was separated and the aqueous layer was lyophilized. The lyophilate was washed (3 times) with 100 ml portions of dichloromethane. These washes were concentrated in vacuo, dissolved in 2 ml of water (pH 4.5) and passed through 10 ml of Dowex 50 resin (K⊕, 0.7 meq/ml) to yield 120 mg of crude product. This was chromatographed through 50 ml of HP-20 resin packed in water; product was eluted with 20% acetone:water. After lyophilization, 62 mg of analytical product was obtained, melting point 175°–180° C., dec.

Analysis Calc'd for $C_{20}H_{25}N_5O_8PK.2.25H_2O$: C, 41.85; H, 5.18; N, 12.20; P, 5.40, Found: C, 42.05; H, 5.01; N, 12.08; P, 5.0.

EXAMPLE 4

Methylphosphonic acid, (S)-2-oxo-3-[(phenylacetyl)amino]-1-azetidinyl ester, potassium salt (S)-N-(1-Hydroxy-2-oxo-3-azetidinyl)-2-phenylacetamide (0.119 g, 0.55 mmole; see U.S. Pat. No. 4,337,197) was dissolved in 3 ml of dry dichloromethane and the solution was cooled to −10° C. under nitrogen. 2,6-Lutidine (0.065 ml, 0.56 mmole) was added, followed by the dropwise addition of a solution of methylphosphonic dichloride in 1 ml of dichloromethane. After addition, the reaction was stirred at −10° C. for 2 hours. The remaining chloro group was hydrolyzed at room temperature with 8 ml of 0.5M $KH_2PO_4$ containing 0.6 ml of 1N KOH (pH 6.0). The solution was stirred vigorously for 2 hours. The dichloromethane layer was separated and the aqueous layer was lyophilized. The lyophilate was washed 3 times with 100 ml portions of dichloromethane and with 100 ml of ethanol. These washes were concentrated in vacuo, combined and dissolved in 2 ml of water. The pH of this solution was adjusted to 4.5 with 1N KOH from pH 2.5. This material was passed through 8 ml of Dowex resin (K⊕, 0.7 meq/ml) to yield 67 mg of crude product. This was placed on 15 ml of HP-20 resin and product was eluted with water. After lyophilization, 20 mg of analytical product was obtained, melting point 135°–140° C., dec.

Analysis Calc'd for $C_{12}H_{14}N_2O_5PK \cdot H_2O$: C, 40.64; H, 4.56; N, 7.90; P, 8.73, Found: C, 40.64; H, 4.47; N, 7.89; P, 8.4.

EXAMPLE 5

[3S-[3α(Z),4β]]-2-[[[1-(2-Amino-4-thiazolyl)-2-[[1-[(hydroxymethoxyphosphinyl)oxy]-4-methyl-2-oxo-3-azetidinyl]amino]-2-oxoethylidine]amino]oxy]-2-methylpropanoic acid, dipotassium salt (A) Methylphosphoric acid, [3S-(3α,4β)]-3-[[(1,1-dimethylethoxy)carbonyl]amino]-4-methyl-2-oxo-1-azetidinyl ester, potassium salt

[3S-(3α,4β)]-3-[[(1,1-Dimethylethoxy)carbonyl]amino]-4-methyl-2-oxo-1-hydroxyazetidine (1.18 g, 5.46 mmole, see example 1D) was partially dissolved in 14 ml of dry dichloromethane and cooled to −70° C. under nitrogen. Triethylamine (0.78 ml, 5.46 mmole) was added followed by the dropwise addition of methyl phosphonic dichloride (0.79 g, 5.46 mmole) in 6 ml of dichloromethane. The reaction mixture was stirred for 1.2 hours while warming from −60° to −30° C. A solution of 0.5M $KH_2PO_4$ pH 5.5 buffer (55 ml) was added, and the reaction was stirred vigorously. The reaction flask was removed from the cooling bath and the solution was stirred at ambient temperature for 45 minutes. The pH during this time was maintained at 3.5 to 4.0 by occasional addition of 2N KOH. The aqueous layer was lyophilized. The lyophilate was washed with three 150 ml portions of dichloromethane, and the dichloromethane was concentrated in vacuo to yield the crude triethyl ammonium salt (1.8 g). This was dissolved in water (pH 4.2) and passed through 90 ml of Dowex 50 resin ($K^\oplus$, 0.7 meq/ml) to yield 0.87 g of crude material, which was purified further by chromatography through 100 ml of HP-20 resin packed in water. The product eluted with 20% acetone-water (170 ml) to yield, after lyophilization, 0.22 g of analytically pure material, melting point 143°, dec.

(B) Methylphosphoric acid, [3S-(3α,4β)]-3-amino-4-methyl-2-oxo-1-azetidinyl ester, trifluoroacetic acid salt Methylphosphoric acid, [3S-(3α,4β)]-3-[[(1,1-dimethylethoxy)carbonyl]amino]-4-methyl-2-oxo-1-azetidinyl ester, potassium salt (0.20 g, 0.57 mmole) was suspended in 0.65 ml of dichloromethane and 0.65 ml of anisole. The reaction mixture was cooled to −10° C., and trifluoroacetic acid (1.3 ml) was added. This was stirred at 0° C. for 1 hour. The solution was concentrated in vacuo to a residue, which was evaporated from benzene (twice) to give a viscous oil. This was triturated with ether to give a white solid, which was dried in vacuo.

(C) [3S-[3α(Z),4β]]-2-[[[1-(2-Amino-4-thiazolyl)-2-[[1-[(hydroxymethoxyphosphinyl)oxy]-4-methyl-2-oxo-3-azetidinyl]amino]-2-oxoethylidine]amino]oxy]-2-methylpropanoic acid, diphenylmethyl ester, potassium salt (Z)-(2-Amino-4-thiazolyl)[[2-diphenylmethoxy)-1,1-dimethyl-2-oxoethoxy]imino]acetic acid (0.29 g, 0.66 mmole) and 1-hydroxybenzotriazole (0.10 g, 0.66 mmole) were dissolved in 8 ml of dry dimethylformamide (DMF) nitrogen. This was cooled to 0° C., and N,N-dicyclohexylcarbodiimide (0.14 g, 0.66 mmole) was added portionwise. After addition, the reaction was stirred at 0° C. for 1 hour. Methylphosphoric acid, [3S-(3α,4β)]-3-amino-4-methyl-2-oxo-1-azetidinyl ester, trifluoroacetic acid salt (0.57 mmol) in 2 ml of DMF and 0.5 ml of N,N-diisopropylethylamine were added to the activated acid side chain, and the reaction was stirred overnight at room temperature. The solution was filtered, and the filtrate was concentrated in vacuo. The residue was dissolved in 8 ml of water, and the pH was adjusted to 4.5 with 1N KOH. This solution was passed through 100 ml of Dowex 50 ($K^\oplus$, 0.7 meq/ml) using water, and lyophilized to give 0.202 g of crude material contaminated with hydroxybenzotriazole.

(D) [3S-[3α(Z),4β]]-2-[[[1-(2-Amino-4-thiazolyl)-2-[[1-[(hydroxymethoxyphosphinyl)oxy]-4-methyl-2-oxo-3-azetidinyl]amino]-2-oxoethylidine]amino]oxy]-2-methylpropanoic acid, dipotassium salt

[3S-[3α(Z),4β]]-2-[[[1-(2-Amino-4-thiazolyl)-2-[[1-[(hydroxymethoxyphosphinyl)oxy]-4-methyl-2-oxo-3-azetidinyl]amino]-2-oxoethylidine]amino]-oxy]-2-methylpropanoic acid, diphenylmethyl ester, potassium salt was dissolved in 1.8 ml of dichloromethane, 0.5 ml of anisole, and 1.5 ml of trifluoroacetic acid, and stirred under $N_2$ at −10° C. for 1 hour. The reaction mixture was concentrated in vacuo, and the residue was evaporated from benzene (three times). The residue was washed with ether:ethyl acetate (1:1) and ether:acetonitrile (1:1) to give a white solid. This material was dissolved in 2 ml of pH 5.5, 0.5M $KH_2PO_4$ and the pH was adjusted to 6.5 with 1N KOH. This was chromatographed through 100 ml of HP-20 resin with water to give 77 mg of desired product, melting point 178°-185° C., dec.

Calc'd. for $C_{14}H_{18}N_5SPO_9K_2 \cdot 2.4H_2O$: C, 28.72; H, 3.92; N, 11.96; S, 5.47; P, 5.29, Found: C, 28.72; H, 3.73; N, 11.86; S, 5.51; P, 5.0.

Additional embodiments of compounds following within the scope of this invention are:

[3S-[3α(Z),4α]]-2-[[[1-(2-amino-4-thiazolyl)-2-[[1-[(hydroxymethylphosphinyl)oxy]-4-methyl-2-oxo-3-azetidinyl]amino]-2-oxoethylidene]amino]oxy]-2-methylpropanoic acid, dipotassium salt

[3S-[3α(Z),4α]]-2-[[[1-(2-amino-4-thiazolyl)-2-[[1-(hydroxymethoxyphosphinyl)oxy]-4-methyl-2-oxo-3-azetidinyl]amino]-2-oxoethylidene]amino]oxy]-2-methylpropanoic acid, dipotassium salt methylphosphonic acid, [3S-[3α(Z),4β]]-3-[[(2-aminothiazolyl)(2,2,2-trifluoroethoxyimino)acetyl]amino]-4-methyl-2-oxo-1-azetidinyl ester

[3S-[3α(Z),4β]]-[[[1-(2-amino-4-thiazolyl)-2-[[1-[(hydroxymethylphosphinyl)oxy]-4-methyl-2-oxo-3-azetidinyl]amino]-2-oxoethylidene]amino]oxy]acetic acid methylphosphonic acid, [3S-[3α(Z),4β]]-3-[[(2-amino-4-thiazolyl)[(2-amino-2-oxoethoxy)imino]acetyl]amino]-4-methyl-2-oxo-1-azetidinyl ester methylphosphonic acid, [3S-(3α,4β)]-3-[[(S)-α-[(aminocarbonyl)amino]-2-thiopheneacetyl]amino]-4-methyl-2-oxo-1-azetidinyl ester methylphosphonic acid, [3S-(3α,4β)]-3-[(aminophenyacetyl)amino]-4-methyl-2-oxo-1-azetidinyl ester methylphosphonic acid, [2S-(2α,3β)]-3-[[(phenylsulfo)acetyl]amino]-2-methyl-4-oxo-1-azetidinyl ester methylphosphonic acid, [3S-[3α(Z),4α]]-3-[[(2-amino-4-thiazolyl)(methoxyimino)acetyl]amino]-4-methyl-2-oxo-1-azetidinyl ester

[3S-[3α(Z),4α]]-[[[1-(2-amino-4-thiazolyl)-2-[[1-[(hydroxymethylphosphinyl)oxy]-4-methyl-2-oxo-3-azetidinyl]amino]-2-oxoethylidene]amino]oxy]acetic acid methylphosphoric acid, [3S-[3α(Z),4α]]-3-[[(2-amino-4-thiazolyl)(methoxyimino)acetyl]amino]-4-methyl-2-oxo-1-azetidinyl ester methylphosphoric acid, [3S-[3α(Z),4α]]-3-[[(2-amino-4-thiazolyl)[(2-amino-2-oxoethoxy)imino]acetyl]amino]-4-methyl-2-oxo-1-azetidinyl ester

[3S-[3α(Z),4β]]-2-[[[1-(2-amino-4-thiazolyl)-2-[[1-[(hydroxyphenylphosphinyl)oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[hydroxy(4-methoxyphenyl)phosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[hydroxy(4-dimethylaminophenyl)phosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[hydroxy(phenylmethyl)phosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[[(azidomethyl)hydroxy]phosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[hydroxy(methoxymethyl)phosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[(hydroxyethylphosphinyl)oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[hydroxy(2-propenyl)phosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[(hydroxyphenoxyphosphinyl)oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[hydroxy(4-methylphenoxy)phosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[hydroxy(phenylmethoxy)phosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[(hydroxyethoxy)phosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[(2-fluoroethoxy)hydroxyphosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[hydroxy(methylthio)phosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[(hydroxymethyl)thiophosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[(hydroxyphenyl)thiophosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[(hydroxymethoxy)thiophosphinyl]oxy]-4-methyl-2-oxo-3-azetidinyl]amino]-2-oxoethylidene]amino]oxy-2-methylpropanoic acid

[3S-[3α(Z),4β]]-2-[[[1-(2-amino-4-thiazolyl)-2-[[1-[[(hydroxyphenoxy)thiophosphinyl]oxy]-4-methyl-2-oxo-3-azetidinyl]amino]-2-oxoethylidene]amino]oxy-2-methylpropanoic acid

What is claimed is:

1. A β-lactam having the formula $$R_1-NH-\underset{\underset{O}{\overset{\|}{C}}-N-O-\overset{\underset{OH}{|}}{\underset{}{P}}-R_5}{\overset{R_2}{\underset{|}{C}}\overset{R_4}{\underset{|}{C}}-R_3}\quad \overset{Y}{\underset{}{\|}}$$

or a pharmaceutically acceptable salt thereof, wherein
$R_1$ is an acyl group derived from a carboxylic acid;
$R_2$ is hydrogen or methoxy;
$R_3$ and $R_4$ are the same or different and each is hydrogen, alkyl, alkenyl, alkynyl, cycloalkyl, phenyl, substituted phenyl or a 4, 5, 6 or 7-membered heterocycle, or one of $R_3$ and $R_4$ is hydrogen and the other is azido, halomethyl, dihalomethyl, trihalomethyl, alkoxycarbonyl, 2-phenylethenyl, 2-phenylethynyl, carboxyl, $$-CH_2X_1, -S-X_2, -O-X_2, -O-\underset{\underset{X_5}{|}}{\overset{\overset{X_3}{|}}{C}}-X_4, -S-\underset{\underset{X_5}{|}}{\overset{\overset{X_3}{|}}{C}}-X_4, \text{ or}$$

$$-A-\overset{\overset{O}{\|}}{C}-NX_6X_7;$$

$X_1$ is azido, amino, hydroxy, alkanoylamino, alkylsulfonyloxy, phenylsulfonyloxy, (substituted phenyl)sulfonyloxy, phenyl, substituted phenyl, cyano, $-S-X_2$ or $-O-X_2$;

$X_2$ is alkyl, substituted alkyl, phenyl, substituted phenyl, phenylalkyl, (substituted phenyl)alkyl, alkanoyl, substituted alkanoyl, phenylcarbonyl, (substituted phenyl)carbonyl or heteroarylcarbonyl;

one of $X_3$ and $X_4$ is hydrogen and the other is hydrogen or alkyl, or $X_3$ and $X_4$ when taken together with the carbon atom to which they are attached form a cycloalkyl group;

$X_5$ is formyl, alkanoyl, phenylcarbonyl, (substituted phenyl)carbonyl, phenylalkylcarbonyl, (substitued phenyl)alkylcarbonyl, carboxyl, alkoxycarbonyl, aminocarbonyl, (substituted amino)carbonyl, or cyano;

A is $-CH=CH-$, $-CH_2-CH=CH-$, $-(CH_2)_n-$, $-(CH_2)_{n'}-O-$, $-(CH_2)_{n'}-NH-$, or $-(CH_2)_{n'}-S-CH_2$;

n is 0, 1, 2 or 3;

n' is 1 or 2;

$X_6$ and $X_7$ are the same or different and each is hydrogen or alkyl, or $X_6$ is hydrogen and $X_7$ is amino, substituted amino, acylamino or alkoxy;

$R_5$ is hydroxyl, alkyl, substituted alkyl, phenyl, substituted phenyl, alkoxy, alkylthio, (substituted alkyl)oxy, (substituted alkyl)thio, phenyloxy, phenylthio, (substituted phenyl)oxy or (substituted phenyl)thio; and Y is oxygen or sulfur;

wherein the terms "alkyl" and "alkoxy" refer to groups having 1 to 10 carbon atoms;

the term "cycloalkyl" refers to groups having 3, 4, 5, 6 or 7 carbon atoms;

the terms "alkanoyl", "alkenyl", and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxyl groups;

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, (4, 5, 6 or 7-membered heterocycle)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylimino, benzylimino or substituted alkyl, wherein the alkyl group has 1 to 4 carbon atoms, groups;

the term "a 4, 5, 6, or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylimino, benzylimino or substituted alkyl, wherein the alkyl group has 1 to 4 carbon atoms, groups;

the term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy or amino;

the term "substituted alkanoyl" refers to a group having the formula

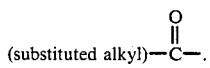

2. A β-lactam having the formula

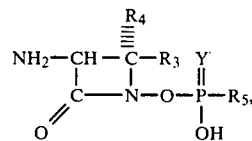

or a salt thereof, wherein $R_3$ and $R_4$ are the same or different and each is hydrogen, alkyl, alkenyl, alkynyl, cycloalkyl, phenyl, substituted phenyl or a 4, 5, 6 or 7-membered heterocycle, or one of $R_3$ and $R_4$ is hydrogen and the other is azido, halomethyl, dihalomethyl, trihalomethyl, alkoxycarbonyl, 2-phenylethenyl, 2-phenylethynyl, carboxyl,

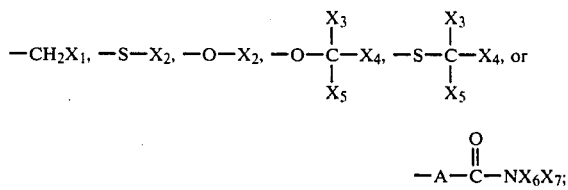

$X_1$ is azido, amino, hydroxy, alkanoylamino, alkylsulfonyloxy, phenylsulfonyloxy, (substituted phenyl)sulfonyloxy, phenyl, substituted phenyl, cyano, $-S-X_2$ or $-O-X_2$;

$X_2$ is alkyl, substituted alkyl, phenyl, substituted phenyl, phenylalkyl, (substituted phenyl)alkyl, alkanoyl, substituted alkanoyl, phenylcarbonyl, (substituted phenyl)carbonyl or heteroarylcarbonyl;

one of $X_3$ and $X_4$ is hydrogen and the other is hydrogen or alkyl, or $X_3$ and $X_4$ when taken together with the carbon atom to which they are attached form a cycloalkyl group;

$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;

A is $-CH=CH-$, $-CH_2-CH=CH-$, $-(CH_2)_n-$, $-(CH_2)_{n'}-O-$, $-(CH_2)_{n'}-NH-$, or $-(CH_2)_{n'}-S-CH$;

n is 0, 1, 2 or 3;

n' is 1 or 2;

$X_6$ and $X_7$ are the same or different and each is hydrogen or alkyl, or $X_6$ is hydrogen and $X_7$ is amino substituted amino, acylamino or alkoxy;

$R_5$ is hydroxyl, alkyl, substituted alkyl, phenyl, substituted phenyl, alkoxy, alkylthio, (substituted alkyl)oxy, (substituted alkyl)thio, phenyloxy, phenylthio, (substituted phenyl)oxy or (substituted phenyl)thio;

Y is oxygen or sulfur;

wherein the terms "alkyl" and "alkoxy" refer to groups having 1 to 10 carbon atoms;

the term "cycloalkyl" refers to groups having 3, 4, 5, 6 or 7 carbon atoms;

the terms "alkanoyl", "alkenyl", and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxyl groups;

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, (4, 5, 6 or 7-membered heterocycle)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylimino, benzylimino or substituted alkyl, wherein the alkyl group has 1 to 4 carbon atoms, groups;

the term "a 4, 5, 6, or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylimino, benzylimino or substituted alkyl, wherein the alkyl group has 1 to 4 carbon atoms, groups;

the term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy or amino;

the term "substituted alkanoyl" refers to a group having the formula

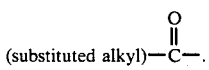

3. A β-lactam in accordance with claim 2 wherein Y is oxygen.

4. A β-lactam in accordance with claim 1 wherein $R_2$ is hydrogen and Y is oxygen.

5. A β-lactam in accordance with claim 4 wherein $R_3$ and $R_4$ are each hydrogen.

6. A β-lactam in accordance with claim 4 wherein $R_3$ is hydrogen and $R_4$ is methyl.

7. A β-lactam in accordance with claim 4 wherein $R_3$ is methyl and $R_4$ is hydrogen.

8. A β-lactam in accordance with claim 4 wherein $R_5$ is alkyl or alkoxy.

9. A β-lactam in accordance with claim 4 wherein $R_5$ is methyl or methoxy.

10. A β-lactam in accordance with claim 4 wherein $R_1$ is (Z)-[(2-amino-4-thiazolyl)(methoxyimino)acetyl].

11. A β-lactam in accordance with claim 4 wherein $R_1$ is (Z)-2-amino-[(1-carboxy-1-methylethoxy)imino]-4-thiazoleacetyl.

12. A β-lactam in accordance with claim 1 wherein Y is oxygen, $R_2$, $R_3$, and $R_4$ are each hydrogen and $R_5$ is methyl.

13. A β-lactam in accordance with claim 1 wherein Y is oxygen, $R_2$ and $R_3$ are each hydrogen and $R_4$ and $R_5$ are each methyl.

14. A β-lactam in accordance with claim 1 wherein Y is oxygen, $R_2$ and $R_4$ are each hydrogen and $R_3$ and $R_5$ are each methyl.

15. The β-lactam in accordance with claim 1, methylphosphonic acid, [3S-[3α(Z),4β]]-3-[[(2-amino-4-thiazolyl)(methoxyimino)acetyl]amino]-4-methyl-2-oxo-1-azetidinyl ester, or a salt thereof.

16. The β-lactam in accordance with claim 1, [3S-[3α(Z),4β]]-2-[[[1-(2-amino-4-thiazolyl)-2-[[1-[(hydroxymethylphosphinyl)oxy]-4-methyl-2-oxo-3-azetidinyl]amino]-2-oxoethylidene]amino]-2-methylpropanoic acid, or a salt thereof.

17. The β-lactam in accordance with claim 1, [3S-[3α(Z),4β]]-2-[[[1-(2-amino-4-thiazolyl)-2-[[1-[(hydroxymethoxyphosphinyl)oxy]-4-methyl-2-oxo-3-azetidinyl]amino]-2-oxoethylidene]amino]oxy]-2-methylpropanoic acid, or a salt thereof.

18. The β-lactam in accordance with claim 3 wherein $R_4$ is hydrogen and $R_3$ and $R_5$ are each methyl, or a salt thereof.

19. The β-lactam in accordance with claim 3 wherein $R_3$ is hydrogen, $R_4$ is methyl and $R_5$ is methoxy, or a salt thereof.

20. A β-lactam in accordance with claim 3 wherein $R_3$ and $R_4$ are each hydrogen, or a salt thereof.

21. The β-lactam in accordance with claim 3 wherein $R_3$ and $R_4$ are each hydrogen and $R_5$ is methyl, or a salt thereof.

22. The β-lactam in accordance with claim 3 wherein $R_3$ is hydrogen and $R_4$ and $R_5$ are each methyl, or a salt thereof.

* * * * *